(12) United States Patent
Aphinyanaphongs et al.

(10) Patent No.: US 7,529,737 B2
(45) Date of Patent: May 5, 2009

(54) CONTENT AND QUALITY ASSESSMENT METHOD AND APPARATUS FOR BIOMEDICAL INFORMATION RETRIEVAL

(76) Inventors: Yin Aphinyanaphongs, 1808 Natches Trace, Nashville, TN (US) 37212; Constantin Aliferis, 320 Boxmere Pl., Nashville, TN (US) 37215

(*) Notice: Subject to any disclaimer, the term of this patent is extended or adjusted under 35 U.S.C. 154(b) by 516 days.

(21) Appl. No.: 11/129,388

(22) Filed: May 16, 2005

(65) Prior Publication Data

US 2005/0289199 A1  Dec. 29, 2005

Related U.S. Application Data

(60) Provisional application No. 60/570,879, filed on May 14, 2004.

(51) Int. Cl.
| | |
|---|---|
| G06F 7/00 | (2006.01) |
| G06F 17/30 | (2006.01) |
| G06E 1/00 | (2006.01) |
| G06E 3/00 | (2006.01) |
| G06F 15/18 | (2006.01) |
| G06G 7/00 | (2006.01) |

(52) U.S. Cl. .................... 707/3; 707/5; 706/20
(58) Field of Classification Search ........... 707/3, 707/5; 706/20
See application file for complete search history.

(56) References Cited

U.S. PATENT DOCUMENTS

| | | | | |
|---|---|---|---|---|
| 6,059,835 | A * | 5/2000 | Bose | 703/19 |
| 6,263,328 | B1 * | 7/2001 | Coden et al. | 707/3 |
| 6,446,061 | B1 * | 9/2002 | Doerre et al. | 707/3 |
| 2001/0049706 | A1 * | 12/2001 | Thorne | 707/530 |
| 2002/0007285 | A1 * | 1/2002 | Rappaport | 705/2 |
| 2002/0029208 | A1 * | 3/2002 | Josephson | 707/1 |
| 2004/0078211 | A1 * | 4/2004 | Schramm-Apple et al. | 705/1 |
| 2004/0153186 | A1 * | 8/2004 | Khurana | 700/98 |
| 2005/0228763 | A1 * | 10/2005 | Lewis et al. | 706/1 |

OTHER PUBLICATIONS

Y. Aphinyanaphongs, et al., "Text Categorization Models for Retrieval of High Quality Articles in Internal Medicine."

* cited by examiner

*Primary Examiner*—Hosain T Alam
*Assistant Examiner*—Van H Ngo
(74) *Attorney, Agent, or Firm*—Dickstein Shapiro LLP

(57) ABSTRACT

A computer-based process retrieves information organized in documents containing text and/or coded representations of text. The process involves obtaining and labeling a selected set of documents, and extracting and selecting features from each document in the selected set. The extracted and selected features are represented, and models are constructed using parametric learning algorithms. The constructed models are capable of assigning a label to each document. The model parameters being instantiated use a first subset of the selected set of documents. Parameters are chosen by validating the corresponding model against at least a second subset of the full document set. The constructed models also are capable of assigning labels and ranks to similar documents outside a selected subset not previously given to the process of model construction.

41 Claims, 5 Drawing Sheets

Figure 2: Filtering Step

CONTENT AND QUALITY ASSESSMENT METHOD AND APPARATUS FOR BIOMEDICAL INFORMATION RETRIEVAL

CROSS-REFERENCE TO RELATED APPLICATIONS

This application claims the benefit of U.S. provisional Appl. No. 60/570,879 filed May 14, 2004, the entire disclosure of which is incorporated herein by reference.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

The definitive source for scientific knowledge needed to guide optimal patient care, management, and biomedical discovery are the biomedical journals and conference proceedings. Starting more than two decades ago, the rate of publication in all medical specialties and research fields has become so high that it is virtually impossible for even the most dedicated professionals to keep up with the thousands of articles published in each field every year. The problem becomes more pressing when one has to care for multiple patients with limited time to spend per patient and perform literature searches under unkindly deadlines.

Ways to address this problem that have been explored so far include: reviews and textbooks, guidelines, and various services that abstract the state-of-the-art knowledge, as well as automatic filters to select the best papers (according to methodological criteria) in broad content categories.

Unfortunately, all these methods have drawbacks: textbooks are typically out of date to a significant degree by the time they are printed; reviews cannot possibly cover all conceivable patient cases, nor is it agreeable in the scientific community how to conduct them in unbiased and non-distorting ways; guidelines address a narrow range of clinical case types, are very labor intensive to produce, and quickly become outdated; on-line and printed abstraction services typically rely on the authority of their editorial boards and represent a tradeoff between authoritative reviews/guidelines and speedier knowledge dissemination in focused areas; finally, automatic filters so far have relied on ad-hoc quality gold standards, labor-intensive construction, and outdated retrieval technologies.

At the same time studies show that 50% of the 100 million U.S. health consumers who are Internet users routinely search for answers to their health-related questions on the web. There are in excess of 10,000 health-related web sites. Very few of them are factually correct, up-to-date, or complete (with respect to some subject). Many sites push some commercial or other agenda that may lead the public astray.

The principal methods developed so far for helping consumers identify high-quality health-related web sites are: (a) the user applies manually for each site one of more than 100 available quality assessment protocols, and (b) citation-related metrics such as PageRank™. Both of these methods have weaknesses: The vast majority of quality assessment protocols have not been validated, and their application is laborious, time consuming, and beyond the abilities of many users, paradoxically including, in particular, those with low educational background, limited time, or who are under health-related discomfort. It is not known how well citation-related metrics filter out the sites that promote unscientific, suboptimal, dangerous and unnecessarily expensive medical modalities. Plenty of anecdotal evidence suggests that Web-related citations do not provide a satisfactory solution to this problem.

BRIEF SUMMARY OF THE INVENTION

The present invention provides, in an exemplary embodiment, a computer-based process for retrieving information organized in documents containing information organized as text, meta-data, citation information and potentially other types of information. The process includes obtaining and labeling a selected set of documents of any topic, and extracting and selecting features from each document in the selected set. The extracted and selected features are represented, and models are constructed using parametric learning algorithms. The constructed models are capable of assigning a label to each document, and the model parameters are instantiated using a first subset of the selected set of documents or by other principled manners. Parameters are chosen by validating the corresponding model against at least a second subset of the full document set. The constructed models also are capable of assigning labels to similar documents outside a selected subset not previously given to the process of constructing models.

DETAILED DESCRIPTION OF THE INVENTION

Figure 1:
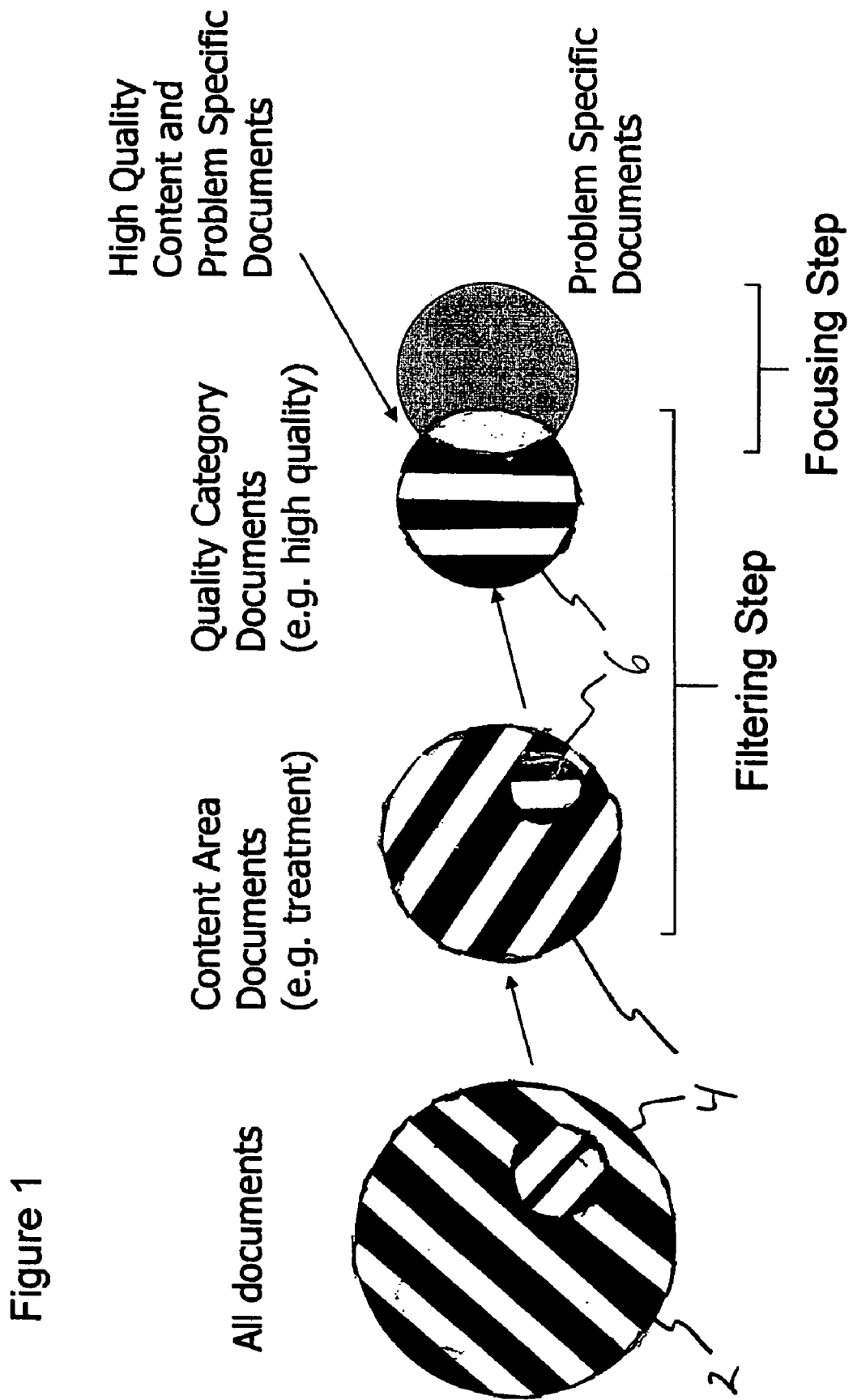
FIG. 1 illustrates high-level functionality of an exemplary embodiment of the present invention.

Referring initially to FIG. 1, high-level functionality is illustrated in an exemplary embodiment of the invention. The invention provides filtering models, and methods to build filtering models, that extract, from the space of all available documents 2, sets of content-area documents 4 that satisfy specific criteria related, for example, to semantics. The sets may be selected or further refined by extracting sets of quality category documents 6 (e.g., describing treatment studies in internal medicine that are of high methodological quality). For further details in selecting a gold standard corpus and other features of the invention, see the "JAMIA paper," Aphinyanaphongs Y, Tsamardinos I, Statnikov A, et al. Text Categorization Models for High Quality Article Retrieval in Internal Medicine. J Amer Med Inform Assoc. 2005; 12(2): 207-216, the entire disclosure of which is incorporated herein by reference.

The invention is further exemplified by use of the filtering models as components in an information-retrieval system, for example, which may carry out problem-focusing and user-interfacing functions by further extracting problem-specific subsets of the filtered-document sets (e.g., if the problem is to treat a patient with peptic ulcer, the subset returned is the intersection of two classes of documents: all documents mentioning treatments of peptic ulcer, and high-quality treatment-related articles).

The filtering models can but do not necessarily assign class membership. The filtering models typically return a ranking score whose semantics may imply that the higher the score the more likely is the document to belong to a target class (one of which, in the example above, would be high quality, treatment-related articles).

Figure 2:
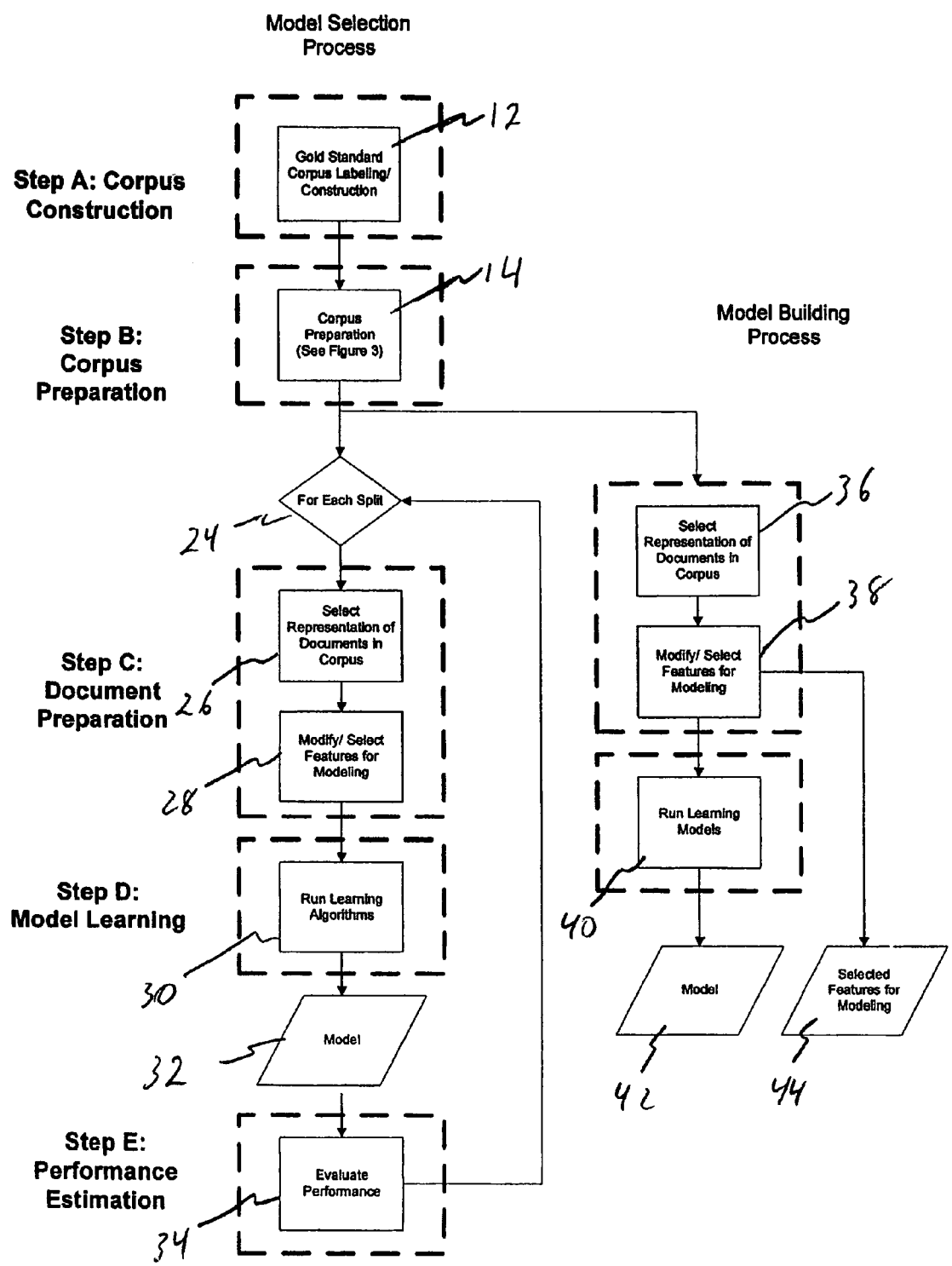
FIG. 2 summarizes the process of creating filtering models according to an exemplary embodiment of the present invention.

Process and Apparatus to Create Filtering Models:

Referring now to FIG. 2, the process of creating filtering models according to an exemplary embodiment of the invention can be summarized as follows:

Corpus Construction

First, a gold-standard set of documents ("corpus") 10 (FIG. 3) is selected at step 12. The corpus documents may be those identified by desired target-class labels. An example of such a target-label is "high-quality article in internal medicine related to prognosis of disease." Such labels can be assigned either manually or automatically. The labels could be negative and positive, where a positive label indicates a document is within the desired target-class and a negative label indicates the document is outside the desired target-class.

Corpus Preparation for Cross Validation

Figure 3:
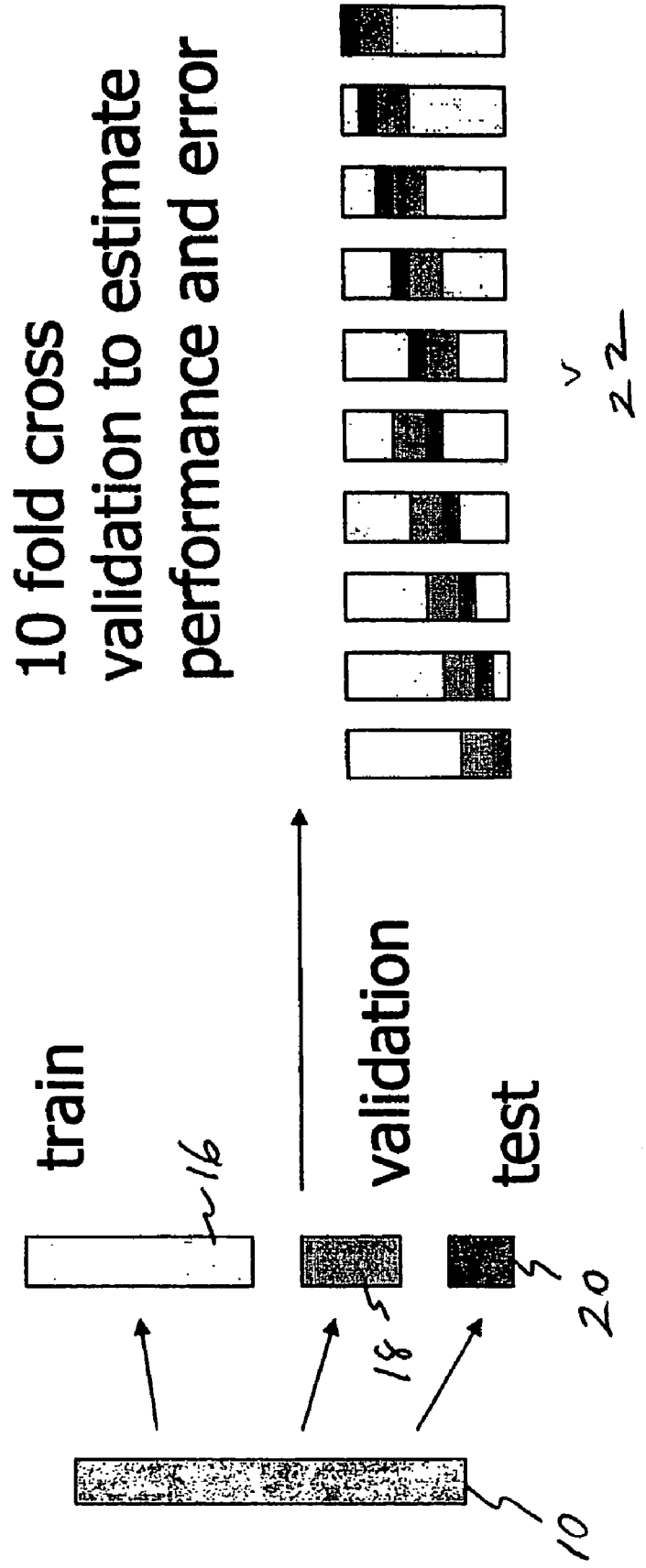
FIG. 3 illustrates one example of how the cross-validation procedure operates according to an exemplary embodiment of the present invention.

Next, the processed corpus documents are split into three sets at step 14: training 16, validation 18, and test 20, as illustrated in FIG. 3. The test set 20 is created and removed while the remaining documents of the original set are further subdivided into a training set 16 and a validation set 18. In one embodiment, the training set 16 comprises 50% of the corpus, the validation set 18 comprises 30% of the corpus, and the test set 20 comprises 20% of the corpus. In another embodiment, 20% of the corpus is set aside as the test set. Of the remaining 80% of the corpus, the training set comprises 70% and the validation set comprises 30%. The training sets 16 are used to build filtering models, the validation sets 18 are used to optimize any specific parameters for the parametric learning algorithms that build the filtering models, and the test sets 20 are used to measure the performance of the best model on previously unseen documents.

The data-splitting procedure at step 14 may be iterated several times to ensure that the filtering models selected and their estimated performance are not a by-product of a particularly favorable or bad split of the data. Each iteration mixes the training, validation, and test splits in a cross-validation procedure 22. However, the union of the test sets 20 of all the splits will be the entire document collection 10. In addition, within each split the proportion of documents with a particular label in the training set 16, validation set 18, and test set 20 is maintained. The exemplary embodiment of the cross-validation procedure illustrated in FIG. 3 is one in which the corpus 10 is split into 10 folds. Several variants can also be employed as explained in more detail below.

Document Representation

Referring back to FIG. 2, within each data-split 24 a representation is chosen at step 26 for each document. One such representation used specifically in an exemplary embodiment of the invention (i.e., the content-quality models for internal medicine articles) is a "bag of words" approach where each document is split into individual words (also called "features" or "terms"). As represented at step 28, features may be modified (via stemming), removed (via application of a "stop word" list), or substituted with other words (by identifying synonyms or broader terms found in thesauri) to prepare the content of the document for application of parametric learning algorithms run at step 30. Examples of parametric learning algorithms include but are not limited to naïve Bayes, neural networks, support vector machines, decision trees, nearest neighbors, Bayesian based algorithms, or the above algorithms with boosting or bagging. Features may also be weighted with schemes that provide measures of relative-importance in making the correct labeling (e.g., "log frequency with redundancy"). Performance of the model obtained at step 32 is evaluated at step 34.

The cross-validation procedure used to estimate performance in the exemplary internal-medicine quality-content embodiment will be described in further detail with reference to FIG. 3. As previously noted, the entire document collection (corpus) 10 is split into three evaluation sets: a train set 16, a validation set 18, and a test set 20 through 10 iterations, in totality across all 10 train 16, validation 18, and test sets 20, the union of the sets 16, 18, 20 equals the entire document collection 10. Performance estimates are made for each of the 10 individual iteration splits. The 10 estimates are averaged or combined for a composite performance measure. The filtering model with the best performance is selected for that quality category task, and subsequent queries for the specific quality and category are executed using this best-performance model. The cross-validation procedure is fully-described in the JAMIA reference, incorporated by reference above.

Model Performance Estimation

The process of generating the best-performance filtering model is distinct from the process of estimating its future performance in unseen cases. This is because estimating future performance requires an additional cross-validation layer that reduces the available sample for training. Hence, once performance of the process that generates the best model is estimated, a test set is no longer needed: the train and validation set are joined into a new training set, and the previous test set becomes a new validation set. Thus, the training sample size is increased for creating the final filtering model. When n-fold cross-validation is used, the best parameters are the ones that are best on the average over all n-fold splits. Hence, as depicted in FIG. 2, the filtering model process consists of two major sub-processes. The first sub-process, steps 24-34 described above, estimates the best-performance filtering-model's future performance for the chosen target-labeling, while the second sub-process, steps 36-44 creates the actual best-performance model. Thus, the best-performing model is obtained by a similar process in which documents are selected from the corpus 10 at step 36 and features are selected at step 38. The model is run at step 40. The model 42 is obtained, as well as selected features for modeling 44. The two sub-processes can run simultaneously, as illustrated in FIG. 2. Alternatively, the second sub-process for creating the actual model can be run after the first sub-process determines the best-performance model.

An exemplary filtering-model generating-process includes application of feature selection methods alone or in combination with symbolic-learning methods (e.g., decision-trees induction). These are useful as follows:

(a) To explain to the end user why the content-quality filters classify documents the way they do (which may be infeasible or computationally intractable with "black box" classifiers such as support vector machines (SVMs) and neural networks (NNs)).

(b) To convert the filter models to queries that can be used by standard Boolean-query search-interfaces.

(c) To examine hidden biases of the creators of the gold standard corpora.

The JAMIA paper incorporated by reference above provides details of how feature selection methods are applied in the internal medicine content-quality embodiment of the invention. Other exemplary embodiments are discussed in the "Variations" section below.

An exemplary process for creating the filtering models is implemented as a collection of software programs that can be run automatically on appropriate document corpora.

Figure 4:
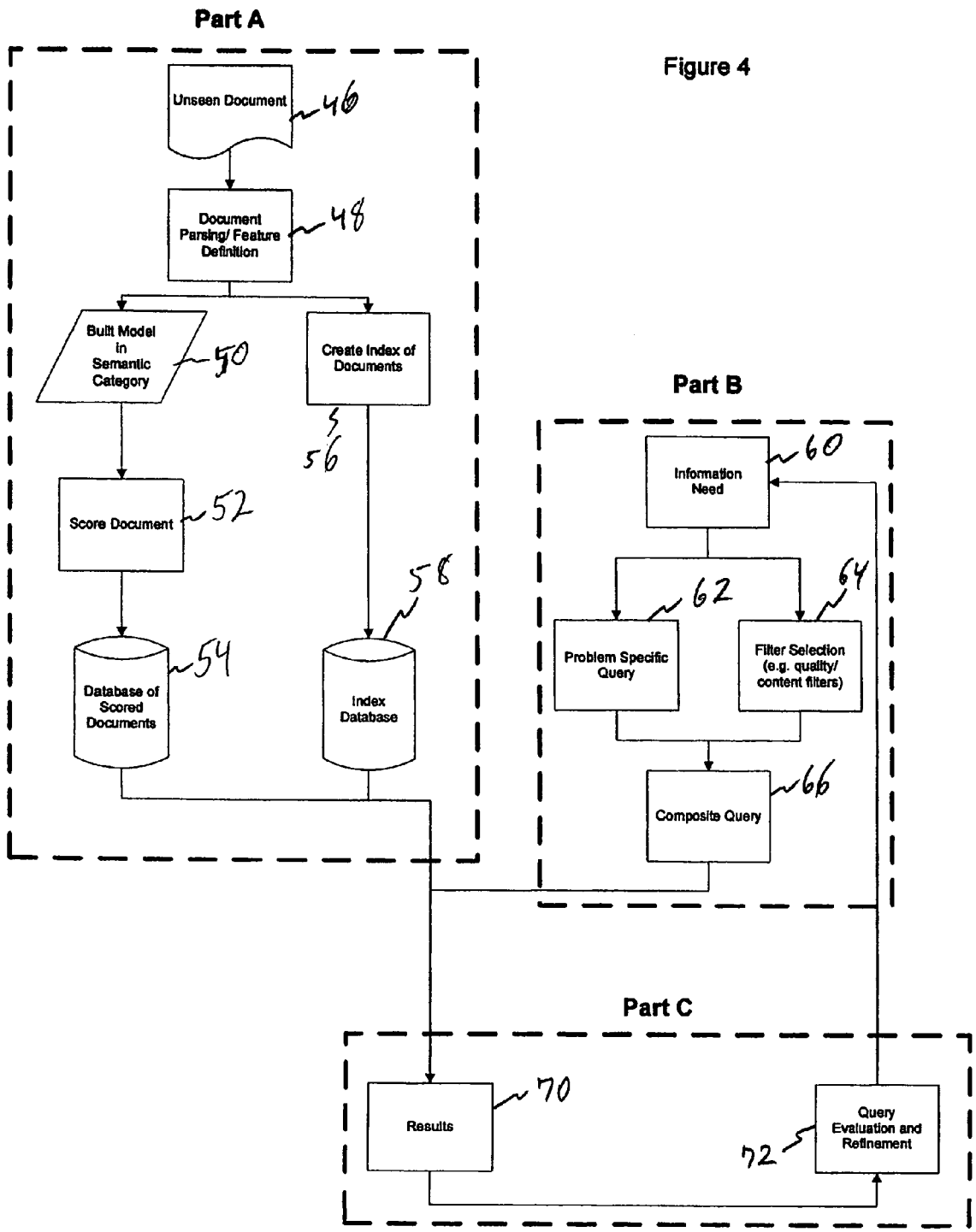
FIG. 4 illustrates the use of the filtering models in an information retrieval system that implements the focusing step according to an exemplary embodiment of the present invention.

FIG. 4 illustrates the use of the filtering models in an information retrieval system that implements an exemplary focusing step of the invention and gives access of the resulting documents to the end user. The system is conceptually divided into three components: Parts A, B, and C.

Component Part A applies the filtering models and stores the results for each document in the document collection so that scores can be retrieved efficiently. As shown in FIG. 4, an unseen document 46 is subjected to document parsing/feature definition at step 48. The process continues by running the processed document against a built model at step 50, scoring the document at step 52, and storing the document in a database of scored documents 54. Part A processes also include the creation of a document index at step 56, which is stored in an index database 58 the. In a variation of the Part A component, rankings are not pre-computed but are applied in run-time. In another variation the original best model is not applied but a simplified Boolean query is applied to a standard search engine or other database that can give access to the document collection via a Boolean query interface.

Component Part B accepts a user query at step 60 that conveys information about (a) the problem specifics (e.g., patient disease of interest) at step 62, and (b) content/quality requirements (e.g., user wishes to retrieve diagnosis-related documents of high methodological quality only) at step 64. These pieces of information form the composite query 66 submitted to Part A. The query may be a natural language, Boolean based, or form-field based formulation.

Component Part C receives the returned set of documents 70 that are ranked highly by the models and displays them to the user. This component is also responsible for providing the user with explanations of why the filtering model ranks documents the way it does, and may also receive relevance feedback from the user for evaluation and refinement at step 72.

Figure 5:
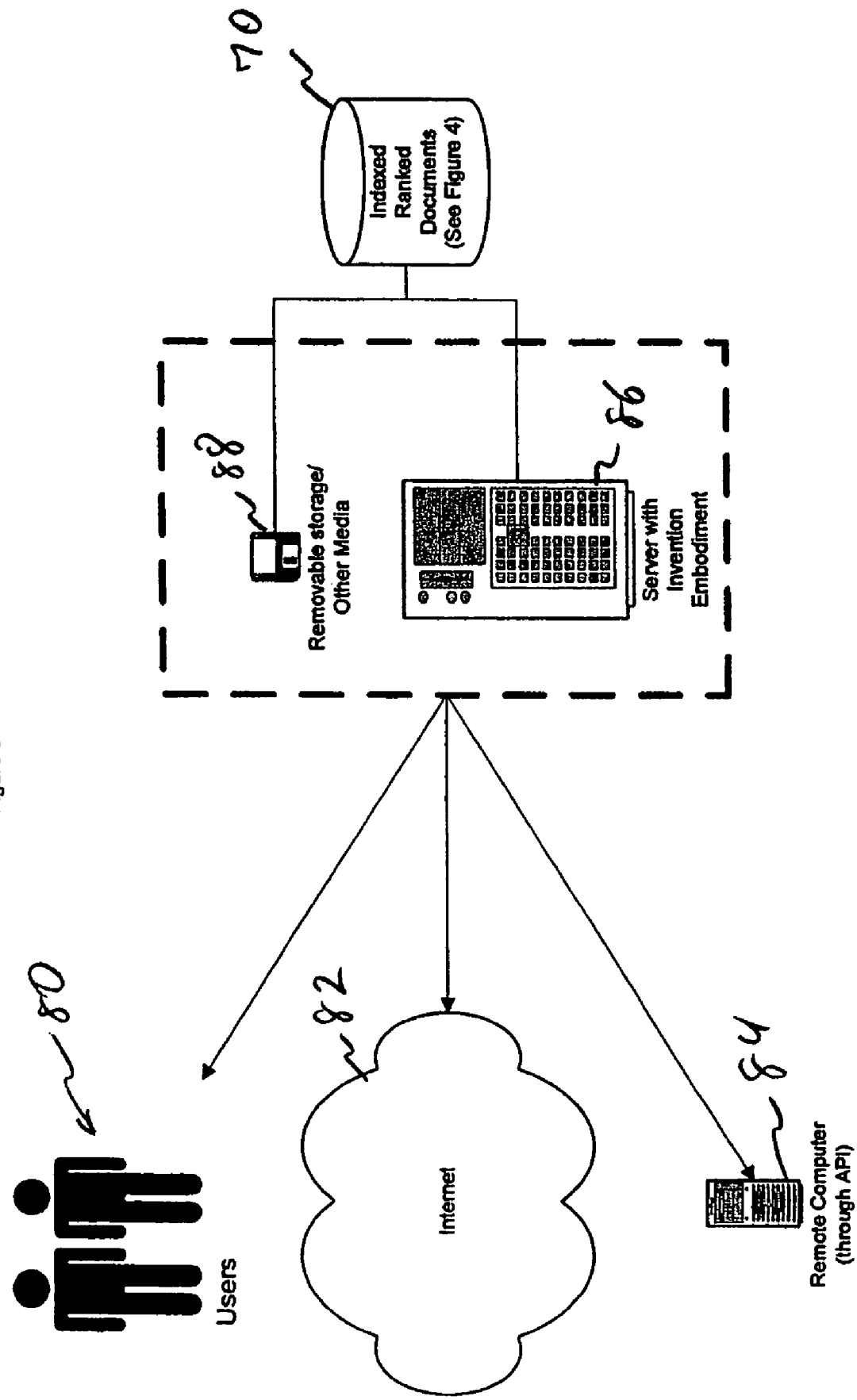
FIG. 5 illustrates application of the invention in a broader context of users by way of the Internet and other remote and/or portable computers according to an exemplary embodiment of the present invention.

FIG. 5 illustrates the application of the invention in the broader context of users 80, the Internet 82, and other remote and/or portable computers 84, without limitation. The invention may reside and/or operate on a server 86 or other media 88, for example. Users 80 may interact directly with the server 86 or other media 88, through the Internet 82, or through an API from a remote computer 84, for example, to obtain information from the indexed ranked document results 70. The invention may also reside on an individual computing platform.

The following describes features of the present invention differ from other prior work in several distinct and key ways in order to further illustrate the invention:

Differences between the present invention and the state of the art are described as the latter is represented by PubMed's clinical query filters (CQFs). The invention as exemplified improves on the state-of-the-art method in several ways: (a) The invention automatically builds and labels a gold standard corpus 10 based on pre-existing published reviews, such as those by the ACP journal club, for example. In contrast to the present invention, the CQFs required manual construction and labeling of articles. (b) The invention relies on no explicit term selection whereas the CQFs require the interviewing of expert searchers and health professionals to find a restricted list of terms. (c) The invention uses sophisticated pattern recognition techniques to build non-Boolean based filtering models. The clinical query filters relied instead on an (inefficient and low-performance) brute force based search of limited-length term disjunctions. (d) The invention reduces the risk of over-fitting the training data through application of cross-validation to determine the best-performance model. The CQFs use one training split without validation sets to determine the best Boolean model to use. Consequently, there is no guarantee that the discovered Boolean model is not over-fitted to the single test split. Using the ACPJ as the gold standard, the internal medicine filters embodiment of the present invention outperforms the CQFs across several standard performance metrics.

A comparison of the present invention was made against relevant prior work of Nwosu, Bachmann, and Shojania in solving quality-related information retrieval problems in biomedical fields. Similarly to the CQFs, the three authors relied on manual construction and labeling of documents in obstetrics and gynecology, for systematic review articles, and in internal medicine respectively. Nwosu and Shojania conducted manual feature selection to select terms while Bachmann used a frequency analysis to do the same. Bachmann's technique required human intervention to select the terms for the disjunctive searches. No method employed feature selection to validate the training corpora, or explain the results to users. In all cases, the Boolean disjunctions were tested on one split of the data (without validation sets), thus risking over-fitting of the discovered queries to the data. Finally, all the studies are limited to Boolean disjunctive representations and no prior work uses a method that ranks documents (as opposed to rigidly classifying them to classes). An expanded discussion of past work and differences can be found in the JAMIA paper.

A potentially large number of exemplary embodiments of the present invention can be obtained, examples and features of which follow:

(a) In the medical field, for example, use can be made of many available and conceivable gold standards including (but not limited to): inclusion/ranking by the Cochran Collection, ranking by the Society of Surgical Ontology Corpus, relevance judgments in the Cystic Fibrosis Collection, inclusion or citation by the journal EBM, published evaluations of books by specific reviewers, or a set of collaborative filtering judgments for a set of documents, or compiled set of documents selected according to personal criteria. For example, a user may define a gold standard for documents discussing drug-drug interactions. The choice and quality of the gold standard will determine the specific focus and applicability of the corresponding embodiment. For example, by using a cancer-related corpus, the invention would be applicable to oncology information retrieval instead of internal medicine, and so on.

(b) The specification of labels for the gold standard need not be dichotomous. Labels from several gold standards may be combined and models built to differentiate amongst several labels. Labels may also be limited to a single class label, and methods devised to automatically estimate degree of difference from this class.

(c) Classification is not accomplished via binary classification but via multi-category classification.

(d) The features for representing the documents are varied: This variation may include using only the title and abstract terms, but not Mesh terms, or using the full text of documents.

Features may also be constructed by other locations of occurrence besides title and abstract. For example, features may be organized as beginning in the first third of an abstract, middle third, or final third.

(e) Cross-validation is accomplished via bootstrapping, leave-one-out, or holdout methods. Cross-validation is also not limited to exactly 10 folds, but may encompass any number of folds from 1 to the number of documents in the corpus.

(f) Machine learning and feature selection methods used may include other established such methods.

(g) The non-probabilistic output of content-quality classifiers is converted to probabilities using standard probability fitting methods.

(h) Application-specific misclassification matrices or evaluation metrics are used to guide the development of best classifiers.

(i) The representation of documents is not a bag of terms but each document may also be pre-processed by natural language processing techniques. These existing methods include negation detection, sense disambiguation, automatic mapping to the UMLS (or other appropriate canonical language); in addition several existing representations that preserve term order may be employed such as ordered term lists, term positions, HMMs, context-sensitive classifiers, transformation-based learning, or stochastic grammars.

(j) The user is provided with a visual graph of the expected number of high-quality documents in the next n unseen documents in the sorted document list; this allows the user to decide whether the benefit from inspecting an arbitrary number of documents is worth her time and effort. The estimation of this number is given by the ranked retrieval curve of the gold standard corpus, adjusted for size of the application domain.

(k) The quality is not determined entirely by content analysis but also by combining content with information such as citations, journal, authors, home institution, etc., and using all of the above as predictors to build the filtering models.

(l) The problem focusing step is not achieved via simple Boolean queries but by using statistical or symbolic information extraction methods to pre-extract population characteristics, disease type, treatment, outcome characteristics and other semantic information and index every document with this information so that the problem-specific component of the user query is formulated according to a well-defined set of parameters. For example, each document can be indexed by what diseases and what types of patient populations (e.g., age, location, race, etc.) it addresses. Then the user is provided with a set of choices limited to the identified diseases and patient characteristics. Once the query of patient type and disease is combined with the desired semantic and quality category, the system can apply the filtering models to return the desired problem-specific set of documents ranked by content and quality.

(m) Documents are arranged in a citation graph that is then post-processed by the filtering models so that only a significantly simplified citation graph containing only high-quality documents remains.

(n) An automated query filtered by the invention filtering models is generated each time a user interacts with a clinical information system to enter coded or free-text information about a patient or population of patients. For example, each time a physician enters a possible diagnosis of myocardiopathy, all the latest high-quality articles related to diagnosis and treatment of that disease category, that have not been seen by this physician in the past, can be automatically made available for inspection.

(o) The user feedback collected by component Part C of the information retrieval part of the invention can be used by component Part A as an additional predictor for building filtering models.

(p) Clustering methods can further organize the results into coherent subgroups of documents; automatic identification of prominent keywords can characterize the contents of each automatically-created cluster.

(q) Other exemplifications of the invention can employ different canonical languages and related browsers than Mesh and the NLM Mesh browser for formulation of Boolean queries by the user. Such browsers/completers may, for example, allow the composition of queries using term synonyms, partial term entry, spelling errors, term "explosion", and inspection of the MESH/content trees.

(r) The retrieval system builds models specifically tailored to individual user interests or document assessment so that the filtering models are user-specific. For example, the gold standard corpus labels can be specified by a single user and applied only for that user's benefit.

(s) In another variation of the invention, these filters may be employed as a first step to establish the documents that have the highest probability of answering a specific question. Then natural language or other statistical techniques may be used to parse out the answer to a question. For example, a user may ask what the frequency of headaches is in patients preceding a stroke incident. The filters may be used to narrow the selection of articles to choose, and natural language processing techniques to return a specific frequency for this question.

In addition to the explained utility for end users such as health professionals, librarians, and members of the general public searching on the Web, the present invention can be applied, without limitation to:

(a) Enhance all types of Clinical Information Systems. Such information systems include, but are not limited to: Provider Order Entry, Electronic Medical Record, Laboratory Information and Picture Archival Systems.

(b) Enhance intelligent decision support (a.k.a. "Expert") systems, Evidence Based Medicine news and abstraction services, and all kinds of information retrieval systems used in biomedicine.

(c) Enhance public health information resources, such as PubMed Central, the CDC on-line resources, clinical trial databases, etc.

(d) Enhance proprietary or publicly-available guideline systems and repositories.

(e) Enhance search engines and portals (both general ones and ones specializing in biomedicine).

In all of the above applications the invention enhances broader services and systems by linking use of the broader system to high-quality pertinent information that may justify the system's advice, or drive the users' attention to pertinent medical facts.

In addition, the present invention can:

(f) Enhance educational products/services in the Health Sciences, Evidence Based Medicine, Information retrieval Computer Science etc.

(g) Assist in the process of biomedical document indexing (by identifying content categories).

(h) Complement or substitute the widely-used Impact Factor metric for the purpose of assessment of scientific journals and their authors.

According to the above, the invention can be useful to:

(a) Health professionals, biomedical researchers, librarians, healthcare policy makers, editorial board members, healthcare managers, their supporting staff, and health services consumers.

(b) Hospitals, libraries, health services provider groups, insurance companies, and HMOs.

(c) Companies active in medical decision support information technology, Evidence Based Medicine abstraction services, health-specializing or general Web portals, and general or specialized Web search engines.

(d) Public Health and Health System officials and organizations at the city, state, and national levels.

The above description and drawings illustrate preferred embodiments which achieve the objects, features, and advantages of the present invention. Although certain advantages and preferred embodiments have been described above, those skilled in the art will recognize that substitutions, additions, deletions, modifications and/or other changes may be made without departing from the spirit or scope of the invention. Accordingly, the invention is not limited by the foregoing description but is only limited by the scope of the appended claims.

What is claimed as new and desired to be protected by Letters Patent of the United States is:

1. A process performed by a processor for retrieving information organized in documents containing information in the form of text, meta-data, citation information and potentially other types of information comprising the steps of:
   obtaining and labeling a selected set of documents;
   extracting and selecting features from each document in the selected set;
   representing the extracted and selected features;
   dividing the set of documents into a plurality of splits of documents, each split comprising first, second, and third subsets;
   constructing models using a parametric learning algorithm, the constructed models being capable of assigning a label to a document, the models being instantiated using the first subset of a first of the plurality of splits of documents, and parameters associated with the model being chosen by validating the model against the second subset of the first of the plurality of splits;
   repeating the constructing, instantiating, and validating steps for each of the second and subsequent splits in the plurality of splits;
   testing the validated models by applying them to the third subset of a respective split; and
   selecting a best validated model, wherein the best validated model is configured to assign labels to documents exclusive of the selected set of documents.

2. A process according to claim 1, wherein the set of documents and the labels are chosen using a plurality of different sources.

3. A process according to claim 1, wherein the step of representing the extracted and selected features is performed using a plurality of different methods.

4. A process according to claim 1, wherein the step of constructing models includes training at least one learning algorithm using the third subset.

5. A process according to claim 1, wherein the step of validating the models is performed iteratively.

6. A process according to claim 5, wherein the step of validating the models and estimating their performance by applying them on the third subset is performed iteratively.

7. A process according to claim 1, further comprising using feature selection methods and symbolic learning to create explanations and visualizations of how the models label documents.

8. A process according to claim 1, further comprising using feature selection methods and symbolic learning to create simplified equivalents to the models that label documents by means of Boolean queries.

9. A process according to claim 1, wherein the selected set of documents is a pre-existing published document set that relates to evidence based medicine.

10. A process according to claim 1, further comprising interacting with a user or another computer system to respond to user or computer queries.

11. The process of claim 1, wherein the assigning a label step comprises characterizing a document as within a target class or outside a target class.

12. The process of claim 11, wherein the applying step comprises using the validated models to characterize each document in the third subset as within the target class or outside the target class.

13. The process of claim 1, wherein the first subset comprises half of the documents in the set of selected documents.

14. The process of claim 13, wherein the third subset comprises 20% of the documents in the set of selected documents.

15. The process of claim 1, wherein the parametric learning algorithm comprises one or more of a naïve Bayes algorithm, a neural network, a support vector machine, a decision tree, a nearest neighbor algorithm, and a Bayesian-based algorithm.

16. The process of claim 15, wherein the parametric learning algorithm is a support vector machine.

17. The process of claim 1, wherein the parametric learning algorithm is boosted or bagged.

18. A computer comprising a memory storing instructions for a processor to carry out a process of retrieving information organized in documents containing information in the form of text, meta-data, citation information and potentially other types of information comprising the steps of:
   obtaining and labeling a selected set of documents;
   extracting and selecting features from each document in the selected set;
   representing the extracted and selected features;
   dividing the set of documents into a plurality of splits of documents, each split comprising first, second, and third subsets of the documents in the split;
   constructing models using a parametric learning algorithm, the constructed models being capable of assigning a label to a document, the models being instantiated using the first subset of a first of the plurality of splits of documents, and parameters associated with the model being chosen by validating the model against the second subset of the first of the plurality of splits;
   repeating the constructing, instantiating, and validating steps for each of the second and subsequent splits in the plurality of splits;
   testing the validated models by applying them to the third subset of a respective split; and
   selecting a best validated model,
wherein the best validated model is configured to assign labels to documents exclusive of the selected set of documents.

19. A computer according to claim 18, wherein the set of documents and the labels are chosen using a plurality of different sources.

20. A computer according to claim 18, wherein the step of representing the extracted and selected features is performed using a plurality of different methods.

21. A computer according to claim 18, wherein the step of constructing models includes training at least one learning algorithm using the third subset.

22. A computer according to claim 18, wherein the step of validating the models is performed iteratively.

23. A computer according to claim 22, wherein the step of validating the models and estimating their performance by applying them on the third subset is performed iteratively.

24. A computer according to claim 18, further comprising using feature selection methods and symbolic learning to create explanations and visualizations of how the models label documents.

25. A computer according to claim 18, further comprising using feature selection methods and symbolic learning to create simplified equivalents to the models that label documents by means of Boolean queries.

26. A computer according to claim 18, wherein the selected set of documents is a pre-existing published document set that relates to evidence based medicine.

27. A computer according to claim 18, further comprising interacting with a user or another computer system to respond to user or computer queries.

28. A computer containing a processor configured to create models by retrieving information organized in documents containing information in the form of text, meta-data, citation information and potentially other types of information comprising the steps of:
  obtaining and labeling a selected set of documents;
  extracting and selecting features from each document in the selected set;
  representing the extracted and selected features;
  dividing the set of documents into a plurality of splits of documents, each split comprising first, second, and third subsets of the documents in the split;
  constructing models using a parametric learning algorithm, the constructed models being capable of assigning a label to a document, the models being instantiated using the first subset of a first of the plurality of splits of documents, and parameters associated with the model being chosen by validating the model against the second subset of the first of the plurality of splits;
  repeating the constructing, instantiating, and validating steps for each of the second and subsequent splits in the plurality of splits;
  testing the validated models by applying them to the third subset of a respective split; and
  selecting a best validated model,
wherein the best validated model is configured to assign labels to documents exclusive of the selected set of documents.

29. A computer containing a processor configured to create models according to claim 28, wherein the set of documents and the labels are chosen using a plurality of different sources.

30. A computer containing a processor configured to create models according to claim 28, wherein the step of representing the extracted and selected features is performed using a plurality of different methods.

31. A computer containing a processor configured to create models according to claim 28, wherein the step of constructing models includes training at least one learning algorithm using the third subset.

32. A computer containing a processor configured to create models according to claim 28, wherein the step of validating the models is performed iteratively.

33. A computer containing a processor configured to create models according to claim 32, wherein the step of validating the models and estimating their performance by applying them on the third subset is performed iteratively.

34. A computer containing a processor configured to create models according to claim 28, further comprising using feature selection methods and symbolic learning to create explanations and visualizations of how the models label documents.

35. A computer containing a processor configured to create models according to claim 28, further comprising using feature selection methods and symbolic learning to create simplified equivalents to the models that label documents by means of Boolean queries.

36. A computer containing a processor configured to create models according to claim 28, wherein the selected set of documents is a pre-existing published document set that relates to evidence based medicine.

37. A computer containing a processor configured to create models according to claim 28, further comprising interacting with a user or another computer system to respond to user or computer queries.

38. A computer containing a processor configured to create models according to claim 28 that label scientific documents both in and outside the document set that was used to derive the models according to both content and quality in the area of biomedicine.

39. A computer system programmed to carry out a process of retrieving information organized in documents containing information in the form of text, meta-data, citation information and potentially other types of information, the computer system comprising:
  an input/output device configured to receive a set of reference documents;
  a processor configured to:
    extract select documents from the set of reference documents;
    obtain a representation of the selected documents;
    recognize features of the selected documents for modeling;
    divide the selected documents into a plurality of folds, each fold comprising a training subset, a validation subset, and a test subset;
    generate parameters associated with learning algorithms based on the representations of the documents in the training subset of each of the plurality of folds;
    validate the parameters by applying the learning algorithms to the representations of the documents in the validation subset of each of the plurality of folds;
    test the parameters by applying the learning algorithms to the representations of the documents in the test subset of each of the plurality of folds;
    select best parameters; and
    use a learning algorithm having the best parameters to label documents outside the set of reference documents.

40. A computer system according to claim 39, wherein the processor is further configured to generate an indexing system for the selected documents.

41. A computer system according to claim 39, wherein the processor is further configured to alter the features for modeling.

* * * * *